United States Patent
Kamei

(10) Patent No.: US 8,988,600 B2
(45) Date of Patent: Mar. 24, 2015

(54) SUPPORT, IMAGING APPARATUS, AND CONNECTION METHOD FOR AN IMAGING APPARATUS

(75) Inventor: Takatoshi Kamei, Oume (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 54 days.

(21) Appl. No.: 13/599,030

(22) Filed: Aug. 30, 2012

(65) Prior Publication Data

US 2013/0258183 A1 Oct. 3, 2013

(30) Foreign Application Priority Data

Mar. 30, 2012 (JP) ................................ 2012-079181

(51) Int. Cl.
*H04N 5/225* (2006.01)
*H04N 5/232* (2006.01)
*A61B 1/04* (2006.01)

(52) U.S. Cl.
CPC .............. *H04N 5/2253* (2013.01); *A61B 1/04* (2013.01)
USPC ......... 348/374; 348/76; 348/211.14; 600/112

(58) Field of Classification Search
CPC ............ H04N 5/23203; H04N 5/2253; H04N 5/2257; H04N 2005/2255; A61B 1/04; A61B 1/042; A61B 1/05; A61B 1/051; A61B 1/053
USPC .......... 348/65, 66, 67, 68, 69, 70, 71, 72, 73, 348/76, 211.14, 374; 600/109, 110, 112
See application file for complete search history.

(56) References Cited

U.S. PATENT DOCUMENTS

| | | | | |
|---|---|---|---|---|
| 5,220,198 A | | 6/1993 | Tsuji | |
| 5,754,313 A | * | 5/1998 | Pelchy et al. | 358/473 |
| 5,857,963 A | * | 1/1999 | Pelchy et al. | 600/109 |
| 6,313,456 B1 | * | 11/2001 | Miyashita et al. | 250/208.1 |
| 6,494,739 B1 | * | 12/2002 | Vivenzio et al. | 439/579 |
| 6,567,115 B1 | * | 5/2003 | Miyashita et al. | 348/76 |
| 6,635,865 B1 | * | 10/2003 | Soltyk | 250/239 |
| 7,773,122 B2 | * | 8/2010 | Irion et al. | 348/222.1 |
| 7,893,956 B2 | * | 2/2011 | Ayrenschmalz | 348/65 |
| 8,072,537 B2 | * | 12/2011 | Schwarz et al. | 348/374 |
| 8,189,062 B2 | * | 5/2012 | Irion et al. | 348/222.1 |
| 8,602,972 B2 | * | 12/2013 | Unsai | 600/110 |
| 8,821,382 B2 | * | 9/2014 | Kagawa | 600/110 |
| 2007/0008407 A1 | * | 1/2007 | Yamamoto et al. | 348/65 |
| 2008/0117324 A1 | * | 5/2008 | Minamio et al. | 348/340 |

(Continued)

FOREIGN PATENT DOCUMENTS

| | | | |
|---|---|---|---|
| JP | 4-218136 | | 8/1992 |
| JP | 08-307743 | | 11/1996 |
| JP | 10-286229 | | 10/1998 |
| JP | 2000-083896 | | 3/2000 |
| JP | 2001-128935 | | 5/2001 |
| JP | 2006223624 A | * | 8/2006 |
| JP | 2009-027709 | | 2/2009 |

OTHER PUBLICATIONS

Japanese Patent Application No. 2012-079181, Notice of Reasons for Rejection, mailed Jan. 15, 2013, (with English Translation).

*Primary Examiner* — John Villecco

(74) *Attorney, Agent, or Firm* — Blakely, Sokoloff, Taylor & Zafman LLP

(57) ABSTRACT

A support according to an embodiment is a support that supports a wiring board including a mounting area for an image sensor, a first lead area extending from the mounting area and having a first connection terminal formed therein, and a second lead area extending from the mounting area and having a second connection terminal formed therein.

8 Claims, 9 Drawing Sheets

(56) References Cited

U.S. PATENT DOCUMENTS

| | | |
|---|---|---|
| 2009/0021618 A1 | 1/2009 | Schwarz et al. |
| 2009/0027491 A1* | 1/2009 | Irion et al. .................. 348/65 |
| 2009/0259101 A1* | 10/2009 | Unsai .......................... 600/110 |
| 2010/0033559 A1* | 2/2010 | Yasunaga .................... 348/65 |
| 2010/0185052 A1* | 7/2010 | Chang ......................... 600/112 |
| 2011/0249106 A1* | 10/2011 | Makino et al. .............. 348/76 |
| 2013/0314521 A1* | 11/2013 | Satake et al. ............... 348/76 |
| 2014/0009593 A1* | 1/2014 | Segi et al. ................... 348/76 |
| 2014/0094653 A1* | 4/2014 | Lewis et al. ................ 600/109 |

* cited by examiner

SUPPORT, IMAGING APPARATUS, AND CONNECTION METHOD FOR AN IMAGING APPARATUS

CROSS-REFERENCE TO RELATED APPLICATION

This application is based upon and claims the benefit of priority from the prior Japanese Patent Application No. 2012-079181, filed on Mar. 30, 2012; the entire contents of which are incorporated herein by reference.

FIELD

Embodiments described herein relate generally to a support, an imaging apparatus, and a connection method for an imaging apparatus.

BACKGROUND

A conventional imaging apparatus includes a head separated imaging apparatus. The head separated imaging apparatus includes a head unit and a main unit that are separated from each other. The head unit includes an image sensor (e.g., charge coupled device (CCD) image sensor or complementary metal oxide semiconductor (CMOS) image sensor). The main unit processes an image signal sent from the head unit. In recent years, the head unit of the head separated imaging apparatus has become smaller. Therefore, various imaging apparatuses have been proposed in order to downsize the head unit.

DETAILED DESCRIPTION

A support according to an embodiment supports a wiring board including a mounting area for an image sensor, a first lead area extending from the mounting area and having a first connection terminal formed therein, and a second lead area extending from the mounting area and having a second connection terminal formed therein. The support includes a first support surface that supports the mounting area, the first support surface having a first end portion and a second end portion, a second support surface that extends from the first end portion and supports the first lead area, and a third support surface that extends from the second end portion and supports the second lead area. Further, the second support surface and the third support surface are opposed to each other and are formed such that a distance therebetween becomes smaller with increasing distance from the first support surface.

Hereinafter, an embodiment will be described with reference to the drawings.

(Embodiment)

Figure 1:
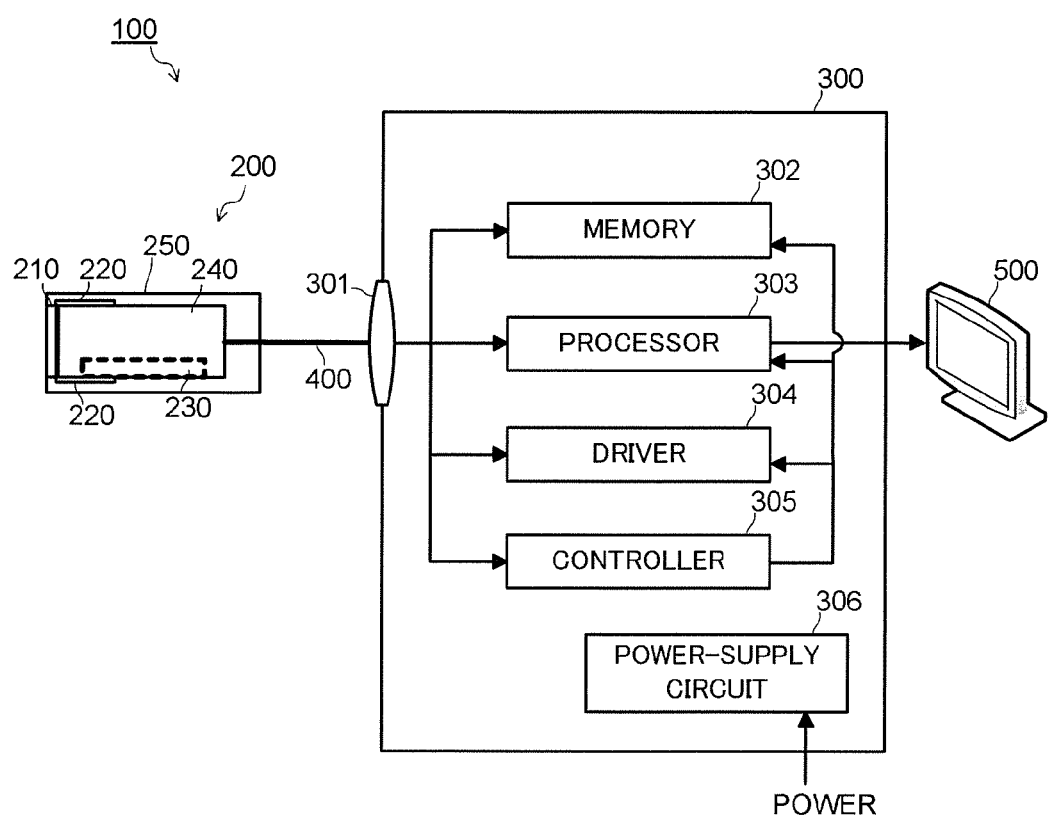
FIG. 1 is a configuration diagram of an imaging apparatus according to an embodiment.

FIG. 1 is a configuration diagram of an imaging apparatus 100 according to an embodiment (hereinafter, referred to as imaging apparatus 100). The imaging apparatus 100 is, for example, an endoscopic apparatus. The imaging apparatus 100 includes a head unit 200, a camera control unit (CCU) 300, and a camera cable 400 that connects the head unit 200 and the CCU 300 to each other.

The head unit 200 includes an image sensor 210, a tape automated bonding (TAB) device 220 (wiring board), a circuit board 230, a base 240, and a casing 250.

The image sensor 210 is, for example, a solid-state image sensor such as a complementary metal oxide semiconductor (CMOS) image sensor or a charge coupled device (CCD) image sensor.

The TAB device 220 is one that has a wiring circuit formed by etching a metal layer laminated on a heat-resistant insulating film. The TAB device 220 is connected to the image sensor 210 via a bump, a bonding pad, or the like.

A driver circuit for the image sensor 210 (e.g., circuit for amplifying output) is mounted on the circuit board 230. The circuit board 230 is connected to connection terminals of the TAB device 220 and to the camera cable 400.

The base 240 supports the TAB device 220 on which the image sensor 210 is mounted and the circuit board 230. The casing 250 houses the image sensor 210, the TAB device 220, the circuit board 230, and the base 240.

The CCU 300 includes an interface (IF) circuit 301, a memory 302, a processor 303, a driver 304, a controller 305, and a power-supply circuit 306.

The IF circuit 301 is an interface for sending and receiving a control signal and data to/from the head unit 200.

The memory 302 is a non-volatile memory, for example, an electrically erasable programmable read-only memory (EEPROM). The memory 302 stores setting data (operation mode) and correction data for the head unit 200.

The processor 303 is a processor for processing an image. The processor 303 performs various corrections (e.g., noise correction, white balance correction, and γ correction) on an image signal sent from the head unit 200. The processor 303 outputs the image signal after the corrections to an external display apparatus 500 (e.g., cathode ray tube (CRT) monitor or liquid-crystal monitor).

The driver 304 is a driver circuit for the image sensor 210. The driver 304 changes a drive system or a frame rate of the image sensor 210 according to control by the controller 305. Further, the driver 304 outputs a pulse signal (e.g., vertical synchronous pulse signal or horizontal synchronous pulse signal (transfer pulse signal, reset gate pulse signal)) to the image sensor 210.

The controller 305 reads out the correction data and the setting data from the memory 302. The controller 305 controls the processor 303 and the driver 304 based on the read-out correction data and setting data.

The power-supply circuit 306 is connected to an external power supply. The power-supply circuit 306 converts an electric power from the external power supply into a predetermined voltage and supplies it to circuit components (IF circuit 301, memory 302, processor 303, driver 304, and controller 305) of the CCU 300. Further, the electric power from the power-supply circuit 306 is also supplied to the head unit 200 via the camera cable 400.

(Configurations of Head Unit 200 and Camera Cable 400)

Figure 2:
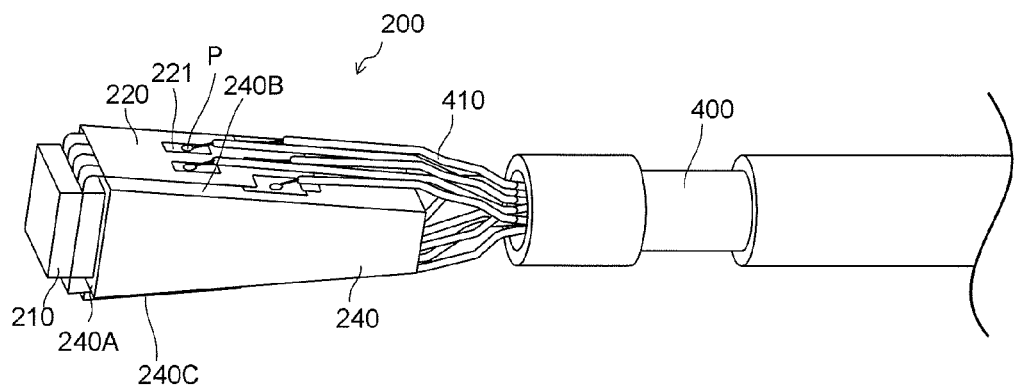
FIG. 2 is a perspective view of a head unit and a camera cable according to the embodiment.
Figure 3:
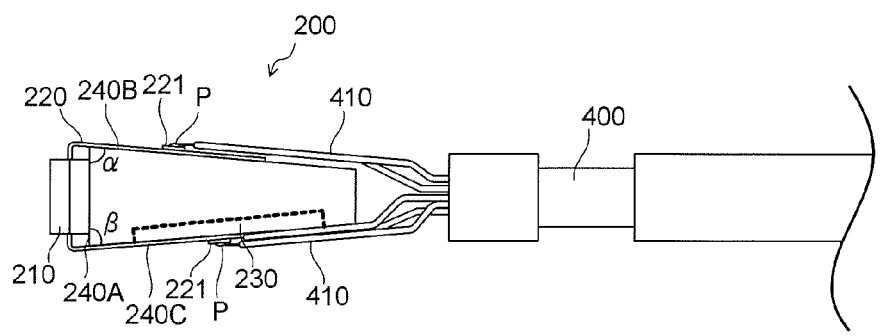
FIG. 3 is a side view of the head unit and the camera cable according to the embodiment.
Figure 4:
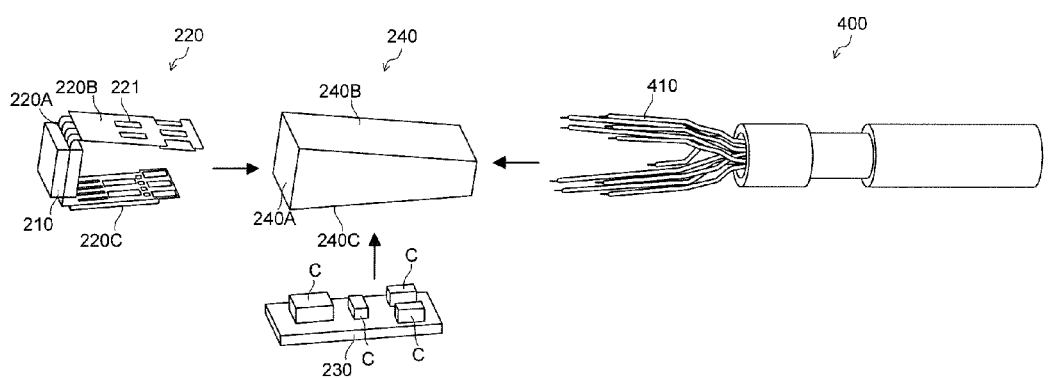
FIG. 4 is an exploded perspective view of the head unit and the camera cable according to the embodiment.

FIG. 2 is a perspective view of the head unit 200 and the camera cable 400. FIG. 3 is a side view of the head unit 200 and the camera cable 400. FIG. 4 is an exploded perspective view of the head unit 200 and the camera cable 400. It should be noted that the casing 250 of the head unit 200 is not shown in FIGS. 2 to 4. Hereinafter, referring to FIGS. 2 to 4, configurations of the head unit 200 and the camera cable 400 will be described.

As shown in FIGS. 2 to 4, the TAB device 220 includes a mounting area 220A and two lead areas 220B and 220C. The image sensor 210 is mounted on the mounting area 220A. The lead areas 220B and 220C extend from the mounting area 220A. Connection terminals 221 are formed in the lead areas 220B and 220C.

The base 240 includes an end surface 240A (first support surface), a top surface 240B (second support surface), and a bottom surface 240C (third support surface). The end surface 240A supports the mounting area 220A of the TAB device 220. The top surface 240B and the bottom surface 240C extend from end portions of the end surface 240A to positions to be opposed to each other and support the two lead areas 220B and 220C of the TAB device 220, respectively. The top surface 240B and the bottom surface 240C of the base 240 form a so-called tapered shape such that a distance therebetween becomes smaller (shorter) with increasing distance from the end surface 240A.

Therefore, as shown in FIG. 3, both of an angle α formed by the end surface 240A and the top surface 240B of the base and an angle β formed by the end surface 240A and the bottom surface 240C of the base are acute angles. Further, the bottom surface 240C of the base 240 is provided with a recess portion for fitting therein the circuit board 230 on which driver circuits C for the image sensor 210 (e.g., circuit for taking out an electric charge from each photoelectric conversion element and converting it into a voltage) are mounted.

The TAB device 220 is supported by the base 240 in such a state that the image sensor 210 is mounted on the mounting area 220A. At this time, the lead areas 220B and 220C of the TAB device 220 are supported on the base 240 in such a state that the lead areas 220B and 220C of the TAB device 220 are folded along the top surface 240B and the bottom surface 240C of the base 240, respectively.

The camera cable 400 houses a plurality of cables 410 for, e.g., data signal (image signal) transmission, synchronous signal (vertical synchronous pulse signal and horizontal synchronous pulse signal) transmission, bias voltage application, electric power supply, and ground (GND). The cables 410 for data transmission and synchronous signal transmission out of the cables 410 housed in the camera cable 400 are coaxial cables.

The TAB device 220 is provided with the plurality of connection terminals 221 for connecting to the cables 410 housed in the camera cable 400. It should be noted that some of the connection terminals 221 are connected to not the cables 410 but connection terminals (not shown) of the circuit board 230. The cables 410 are electrically connected to the connection terminals 221 of the TAB device 220 and the connection terminals of the circuit board 230 with solders P. Alternatively, another method (e.g., silver (Ag) paste) may be used to electrically connect each of the cables 410 housed in the camera cable 400 to each of the connection terminals 221 of the TAB device 220 and the connection terminals of the circuit board 230.

Figure 5:
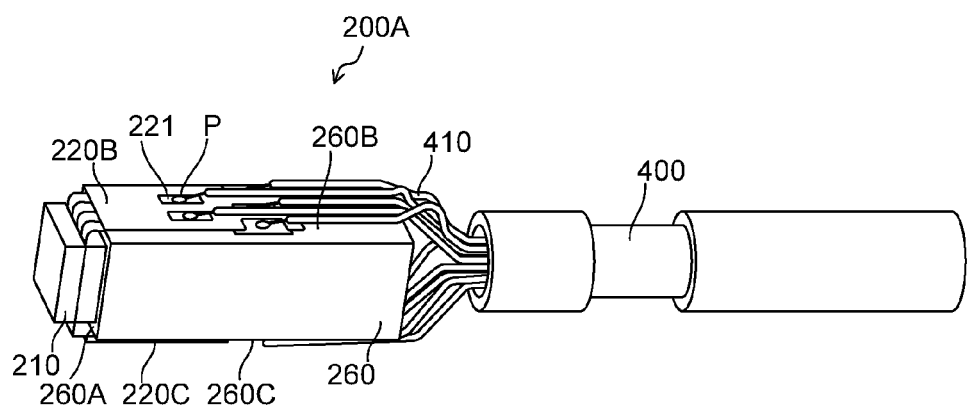
FIG. 5 is a perspective view of a head unit and a camera cable according to a comparative example.

FIG. 5 is a perspective view of a head unit 200A and a camera cable 400 according to a comparative example. A casing of the head unit 200A is not shown in FIG. 5. Hereinafter, referring to FIG. 5, configurations of the head unit 200A and the camera cable 400 will be described. It should be noted that the same configurations as those described with reference to FIGS. 1 to 4 will be denoted by the same reference symbols and duplicate descriptions thereof will be omitted.

As shown in FIG. 5, a base 260 of the head unit 200A according to the comparative example has a cuboid shape. Therefore, a top surface 260B (second support surface) and a bottom surface 260C (third support surface) of the base 260, which respectively support lead areas 220B and 220C of a TAB device 220, are parallel to each other. Thus, a distance between the top surface 260B (second support surface) and the bottom surface 260C (third support surface) of the base 260 does not become smaller (shorter) with increasing distance from an end surface 260A (first support surface) in the head unit 200A according to the comparative example.

Therefore, when each of cables 410 to be housed in the camera cable 400 is soldered to each of connection terminals 221 provided in the lead areas of the TAB device 220, the cables 410 and solders P outwardly protrude from a project plane of the end surface 260A of the base 260 (cuboid with the end surface 260A being a bottom surface). As a result, the head unit 200A is inevitably enlarged by the amount corresponding to the cables 410 and the solders P that protrude from the project plane.

On the other hand, the distance between the top surface 240B (second support surface) and the bottom surface 240C (third support surface) of the base 240, which respectively support the lead areas 220B and 220C of the TAB device 220, becomes smaller (shorter) with increasing distance from the end surface 240A (first support surface) in the imaging apparatus 100 according to this embodiment. Therefore, when each of the cables 410 to be housed in the camera cable 400 is soldered to each of the connection terminals 221 provided in the lead areas of the TAB device 220, the cables 410 and the solders P can be prevented from outwardly protruding from a project plane of the end surface 240A of the base 240 (cuboid with the end surface 240A being a bottom surface). Therefore, the head unit 200 can be downsized.

(Assembling of Head Unit 200 and Camera Cable 400)

FIGS. 6A to 6E are diagrams for explaining how to assemble the head unit 200 and the camera cable 400. Hereinafter, referring to FIGS. 6A to 6E, assembling of the head unit 200 and the camera cable 400 will be described. It should be noted that the casing 250 of the head unit 200 is not shown in FIG. 6E. Further, the same configurations as those described with reference to FIGS. 1 to 4 will be denoted by the same reference symbols and duplicate descriptions thereof will be omitted.

(Preparation of TAB Sheet S)

Figure 6A:
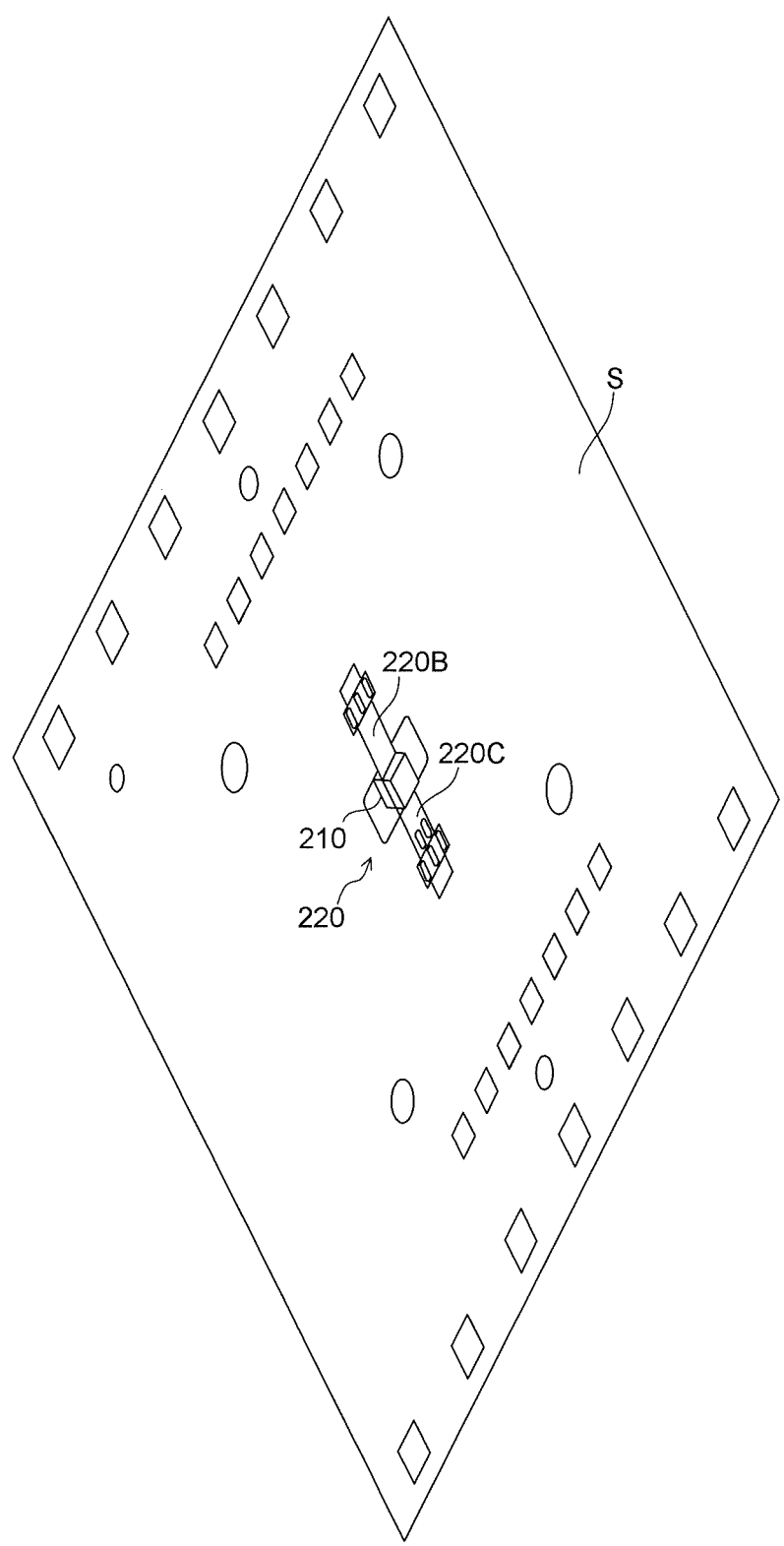
FIGS. 6A to 6E are diagrams for explaining how to assemble the head unit and the camera cable according to the embodiment.

As shown in FIG. 6A, a TAB sheet S in which the image sensor 210 is mounted on the TAB device 220 is prepared.

(Mounting of Base 240)

Figure 6B:
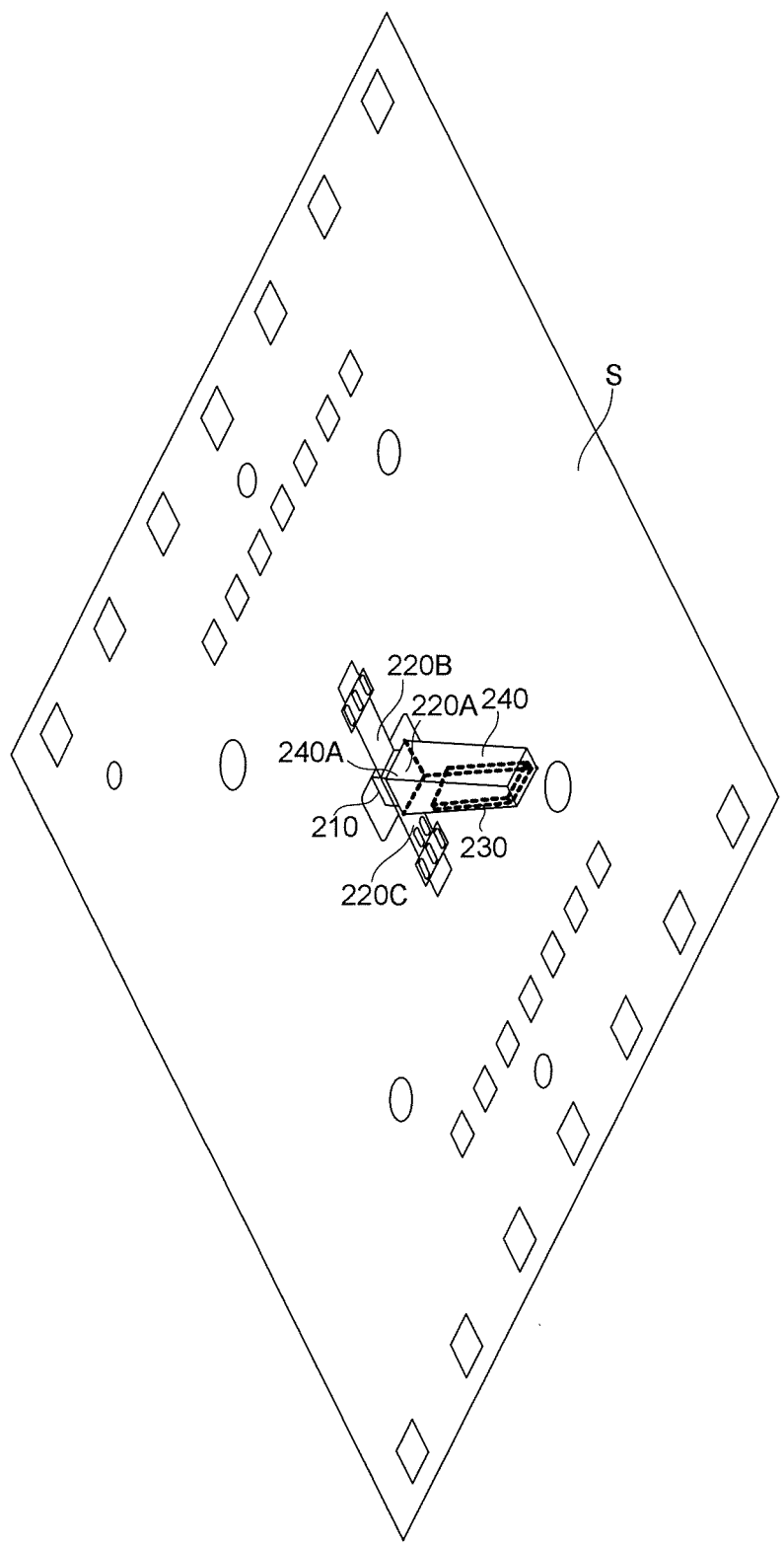

As shown in FIG. 6B, the end surface 240A (first support surface) of the base 240 is mounted on the mounting area 220A of the TAB device 220. At this time, the circuit board 230 has been already mounted on the base 240.

(Cutting Out of TAB Device 220)

Figure 6C:
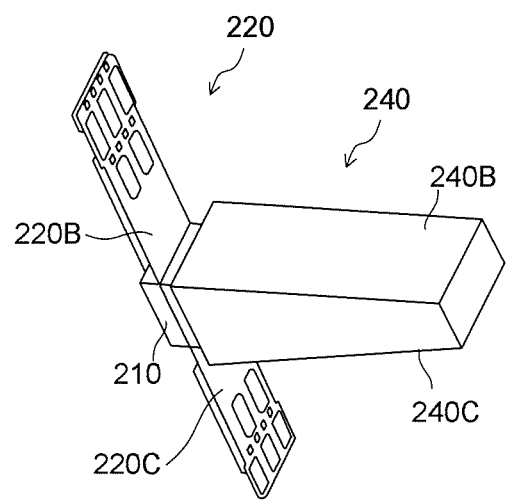

As shown in FIG. 6C, the TAB device 220 is cut out from the TAB sheet S.

(Fitting of TAB Device 220)

Figure 6D:
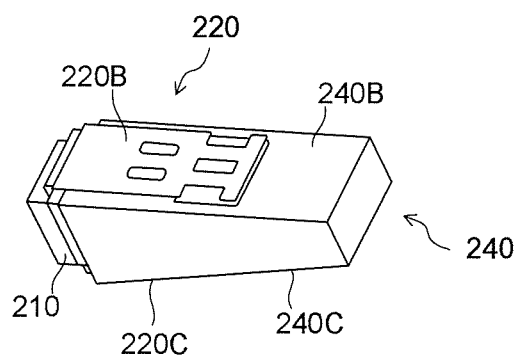

As shown in FIG. 6D, the TAB device 220 is fitted onto the base 240 by folding the lead areas 220B and 220C of the TAB device 220 along the top surface 240B (second support surface) and the bottom surface 240C (third support surface) of the base 240, respectively.

(Connection of Camera Cable 400)

Figure 6E:
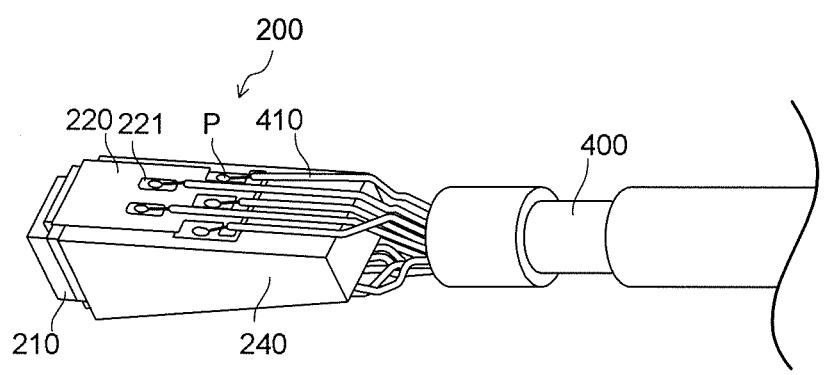

As shown in FIG. 6E, each of the cables 410 to be housed in the camera cable 400 is electrically connected to each of the connection terminals 221 of the TAB device 220 and the connection terminals (not shown) of the circuit board 230 with the solders P. Finally, the casing 250 (not shown) is attached.

As described above, the distance between the top surface 240B (second support surface) and the bottom surface 240C (third support surface) of the base 240, which respectively support the lead areas 220B and 220C of the TAB device 220, becomes smaller (shorter) with increasing distance from the end surface 240A (first support surface) in the imaging apparatus 100 according to this embedment. Therefore, when each of the cables 410 to be housed in the camera cable 400 is soldered to each of the connection terminals 221 provided in the lead areas of the TAB device 220, the cables 410 and the solders P can be prevented from outwardly protruding from the project plane (cuboid with the end surface 240A being the bottom surface) of the end surface 240A of the base 240. Therefore, the head unit 200 can be downsized.

MODIFIED EXAMPLES OF EMBODIMENT

Figure 7A:
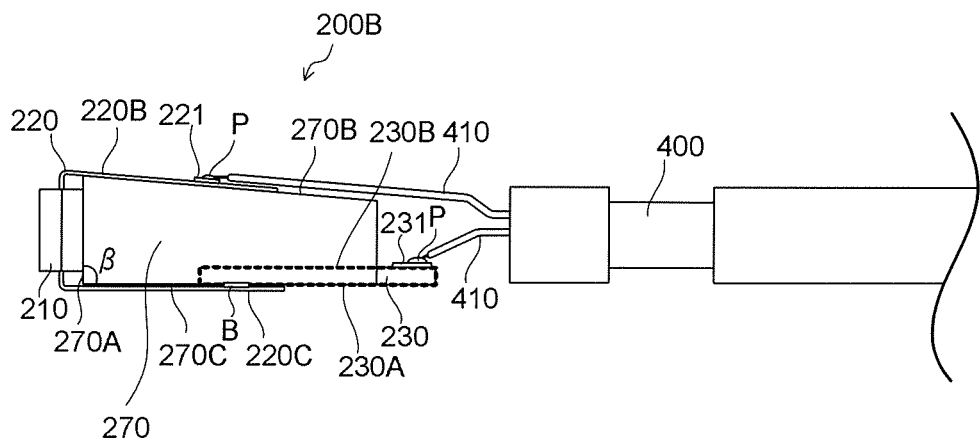
FIGS. 7A and 7B are side views of a head unit and a camera cable according to modified examples of the embodiment.
Figure 7B:
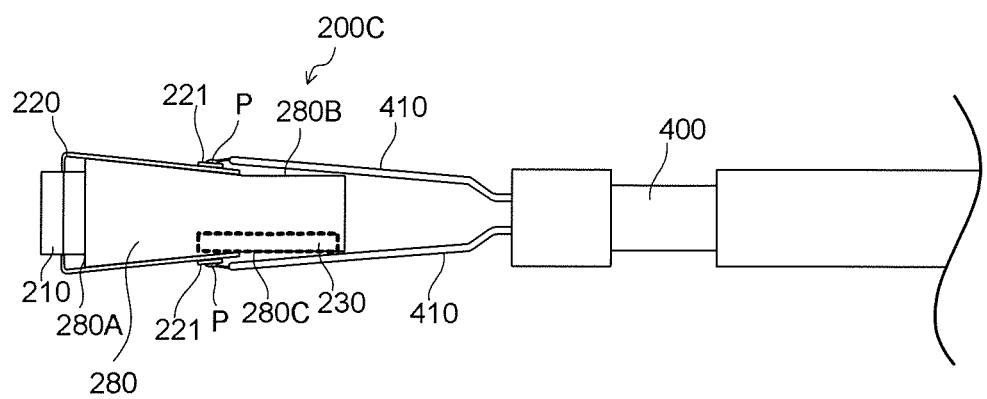

FIGS. 7A and 7B show modified examples of the embodiment. Hereinafter, the modified examples of the embodiment will be described. It should be noted that the same configurations as those described with reference to FIGS. 1 to 6E will be denoted by the same reference symbols and duplicate descriptions thereof will be omitted.

As shown in FIG. 7A, an angle β between a bottom surface 270C (third support surface) of a base 270, on which a circuit board 230 is mounted, and an end surface 270A (first support surface) of the base 270 may be set to be a right angle and connection terminals 221 of a lead area 220C of a TAB device 220 may be connected via the circuit board 230 to cables 410 to be housed in a camera cable 400.

At this time, connection terminals (not shown) of the lead area 220C of the TAB device 220 are connected to a bottom surface 230A side of the circuit board 230 via a bump B or the like and each of the cables 410 is connected to each of connection terminals 231 formed on a top surface 230B side of the circuit board 230. With this configuration, the cables 410 and solders P can be prevented from protruding outside a project plane of the end surface 270A of the base 270 (cuboid with the end surface 270A being a bottom surface). As a result, a head unit 200B can be downsized.

Alternatively, as shown in FIG. 7B, a top surface 280B (second support surface) and a bottom surface 280C (third support surface) of a base 280 may be folded in the middle thereof. Specifically, the top surface 280B (second support surface) and the bottom surface 280C (third support surface) of the base 280 may be configured such that a distance therebetween becomes smaller with increasing distance from an end surface 280A (first support surface) up to the middle thereof and the top surface 280B (second support surface) and the bottom surface 280C (third support surface) become are parallel to each other beyond the middle thereof.

Also with the configuration as shown in FIG. 7B, cables 410 and solders P can be prevented from protruding outside a project plane of the end surface 280A (first support surface) of the base 280 (cuboid with the end surface 280A being a bottom surface). As a result, a head unit 200C can be downsized.

(Other Embodiment)

While certain embodiments have been described, these embodiments have been presented by way of example only, and are not intended to limit the scope of the inventions. Indeed, the novel embodiments described herein may be embodied in a variety of other forms; furthermore, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A support for supporting a wiring board including a mounting area for an image sensor, a first lead area extending from the mounting area and having a first connection terminal formed therein, and a second lead area extending from the mounting area and having a second connection terminal formed therein, the support comprising:

a first support surface configured to support the mounting area, the first support surface including a first end portion and a second end portion;

a second support surface configured to support the first lead area, the second support surface extending from the first end portion of the first support surface; and a third support surface configured to support the second lead area, the third support surface extending from the second end portion of the first support surface, the second support surface and the third support surface being formed to be opposed to each other such that a distance therebetween becomes smaller with increasing distance from the first support surface, wheren the second support surface and the third support surface are formed so that a distance therebetween becomes smaller with increasing distance from the first support surface and the second support surface and the third support surface configured to become parallel to each other in the middle thereof, and wherein the first connection terminal comprises a first electrical pad and a second electrical pad, the first electrical pad and the second electrical pad are adjacently disposed from a line of intersection between the mounting area and the first lead area, where the first electrical pad is disposed a first distance from the line and the second electrical pad is disposed a second distance greater than the first distance from the line.

2. An imaging apparatus, comprising a head unit including an image sensor and a main unit that processes an image signal from the image sensor, the head unit and the main unit being separated from each other, the head unit including:

a wiring board, including:

a mounting area on which the image sensor being mounted;

a first lead area extending from the mounting area and including a first connection terminal formed therein; and a second lead area extending from the mounting area and including a second connection terminal formed therein, wherein the first connection terminal comprises a first electrical pad and a second electrical pad, the first electrical pad and the second electrical pad are adjacently disposed from a line of intersection of the mounting area and the first lead area, where the first electrical pad is disposed a first distance from the line and the second electrical pad is disposed a second distance greater than the first distance from the line, and a support, including:

a first support surface configured to support the mounting area, the first support surface including a first end portion and a second end portion;

a second support surface configured to support the first lead area, the second support surface extending from the first end portion of the first support surface; and a third support surface configured to support the second lead area, the third support surface extending from the second end portion of the first support surface, the second support surface and the third support surface being formed to be opposed to each other so that a distance therebetween becomes smaller with increasing distance from the first support surface, wherein the second support surface and the third support surface are formed so that a distance therebetween becomes smaller with increasing distance from the first support surface and the second support surface and the third support surface configured to become parallel to each other in the middle thereof.

3. An imaging apparatus comprising a head unit including an image sensor and a main unit that processes an image signal from the image sensor, the head unit and the main unit being separated from each other, the head unit including:

a wiring board, including:
- a mounting area on which the image sensor being mounted,
- a first lead area extending from the mounting area and including a first connection terminal formed therein, and
- a second lead area extending from the mounting area and including a second connection terminal formed therein,
- wherein the first connection terminal comprises a first electrical pad and a second electrical pad, the first electrical pad and the second electrical pad are adjacently disposed from a line of intersection of the mounting area and the first lead area, where the first electrical pad is disposed a first distance from the line and the second electrical pad is disposed a second distance greater than the first distance from the line; and a support, including:
- a first support surface configured to support the mounting area, the first support surface including a first end portion and a second end portion,
- a second support surface configured to support the first lead area, the second support surface extending from the first end portion of the first support surface, and
- a third support surface configured to support the second lead area, the third support surface extending from the second end portion of the first support surface, the second support surface and the third support surface being formed to be opposed to each other so that a distance therebetween becomes smaller with increasing distance from the first support surface,
- wherein one of the second support surface and the third support surface comprises a recess portion configured to fit therein a circuit board including a driver circuit for driving the image sensor.

4. A connection method for an imaging apparatus including a head unit including an image sensor and a main unit that processes an image signal from the image sensor, the head unit and the main unit being separated from each other, the method comprising:

mounting the image sensor on a mounting area of a wiring board, the wiring board configured to include the mounting area, a first lead area extending from the mounting area and including a first connection terminal formed therein, and a second lead area extending from the mounting area and including a second connection terminal formed therein;

providing the mounting area to a first support surface of a support, the first support surface comprises a first end portion and a second end portion, the support configured to include the first support surface, a second support surface extending from the first end portion of the first support surface, and a third support surface extending from the second end portion of the first support surface, the second support surface and the third support surface being formed to be opposed to each other so that a distance therebetween becomes smaller with increasing distance from the first support surface and one of the second support surface and the third support surface includes a recess portion configured to fit therein a circuit board that includes a driver circuit for driving the image sensor;

providing the first lead area and the second lead area along the second support surface and the third support surface;

connecting a camera cable, which configured to connect the head unit and the main unit to each other, to at least one of the first connection terminal of the first lead area and the second connection terminal of the second lead area, wherein the first connection terminal comprises a first electrical pad and a second electrical pad, the first electrical pad and the second electrical pad are adjacently disposed from a line of intersection between the mounting area and the first lead area, where the first electrical pad is disposed a first distance from the line and the second electrical pad is disposed a second distance greater than the first distance from the line; and fitting the circuit board into the recess portion.

5. A support for supporting a wiring board including a mounting area for an image sensor, a first lead area extending from the mounting area and having a first connection terminal formed therein, and a second lead area extending from the mounting area and having a second connection terminal formed therein, the support comprising:

a first support surface configured to support the mounting area, the first support surface including a first end portion and a second end portion;

a second support surface configured to support the first lead area, the second support surface extending from the first end portion of the first support surface; and a third support surface configured to support the second lead area, the third support surface extending from the second end portion of the first support surface, the second support surface and the third support surface being formed to be opposed to each other so that a distance between the second support surface and the third support surface reduces with an increased distance from the first support surface, wherein one of the second support surface and the third support surface includes a recess portion configured to receive a circuit board that includes a driver circuit for driving the image sensor.

6. The support according to claim 5, wherein the first connection terminal comprises a first electrical pad and a second electrical pad, the first electrical pad and the second electrical pad are adjacently disposed from a line of intersection between the mounting area and the first lead area, where the first electrical pad is disposed a first distance from the line and the second electrical pad is disposed a second distance greater than the first distance from the line.

7. The support according to claim 5,
wherein the first support surface forms an acute angle with at least one of the second support surface and the third support surface.

8. The support according to claim 5,
wherein the second support surface and the third support surface are formed so that the distance between the second support surface and the third support surface reduces with an increased distance from the first support surface and the second support surface and the third support surface are configured to be in parallel to each other.

* * * * *